United States Patent [19]

Nakayama et al.

[11] 4,408,028

[45] Oct. 4, 1983

[54] OXIDATION-CURABLE EMULSION COMPOSITION CONTAINING A CELLULOSE DERIVATIVE

[75] Inventors: Yasuharu Nakayama; Hiroshi Iwai; Hajime Sukejima, all of Hiratsuka, Japan

[73] Assignee: Kansai Paint Co., Ltd., Japan

[21] Appl. No.: 210,576

[22] Filed: Nov. 26, 1980

[30] Foreign Application Priority Data

Nov. 29, 1979 [JP] Japan ................................ 54-153649

[51] Int. Cl.$^3$ ...................... C08F 2/32; C08F 242/00; C08F 299/00; C08L 1/08
[52] U.S. Cl. ........................................ 526/200; 524/35; 524/37; 524/42; 525/50; 526/319; 526/320
[58] Field of Search ...................... 524/35, 37, 38, 39, 524/40, 41, 42, 46; 525/50; 526/200, 319, 320; 260/17 A, 17 R, 18 PF, 17.4 BB, 17.4 UC, 17.4 GC, 13, 16, 17.4 CL, 22 D, 29.2 UA, 29.6 RW, 22 CB, 23 AR, 23 EM, 23 A, 29.6 WB, 29.6 RB, 29.7 RP, 29.7 W, 29.7 UP; 106/170

[56] References Cited

U.S. PATENT DOCUMENTS

| 3,933,706 | 1/1976 | Momiyama et al. | ........ 260/29.7 UA |
| 3,953,386 | 4/1976 | Murphy et al. | .................. 260/17 A |
| 4,073,758 | 2/1978 | Nakayama et al. | ............ 260/23.7 A |

*Primary Examiner*—John Kight, III
*Assistant Examiner*—Nathan M. Nutter
*Attorney, Agent, or Firm*—Wenderoth, Lind & Ponack

[57] ABSTRACT

An oxidation-curable emulsion composition containing a cellulose derivative, said composition being prepared by polymerizing in emulsion a mixture consisting of at least one radical-polymerizable unsaturated monomer and at least one cellulose derivative in the presence of an oxidation-curable water-soluble resin.

15 Claims, No Drawings

OXIDATION-CURABLE EMULSION COMPOSITION CONTAINING A CELLULOSE DERIVATIVE

This invention relates to an oxidation-curable emulsion composition containing a cellulose derivative. More specifically, it relates to an emulsion composition containing a cellulose derivative in a very stable condition, which when formulated into a coating composition and coated on a substrate, can form a film which is tack-free and has a good feel at its surface and possesses superior properties such as polishability, gloss and gasoline resistance.

The oxidation-curable emulsion composition containing a cellulose derivative in this invention is a polymer emulsion which contains a water-soluble resin having oxidation-curable atomic groupings in the molecule as a dispersion stabilizer, a polymer prepared by radical polymerization of a radical-polymerizable monomer in an aqueous medium in the presence of the oxidation-curable water-soluble resin, and a cellulose derivative.

The term "oxidation-curable atomic groupings", as used herein, denote atomic groupings containing a carbon-carbon double bond, for example a conjugated or non-conjugated carbon-carbon double bond contained in a drying or semi-drying oil, or a carbon-carbon double bond of a 1,4-cis, 1,4-trans or 1,2-vinyl structure contained in a large quantity in polybutadiene.

Various attempts have been made in the past to obtain an emulsion composition by polymerizing at least one radical-polymerizable unsaturated monomer in emulsion using a water-soluble resin as a dispersion stabilizer. This type of emulsion composition is characterized by the fact that it obviates the use of anionic, cationic or nonionic low-molecular or high-molecular surface-active substances which are normally employed in the art for emulsion polymerization. This emulsion has the advantage that a coated film prepared from it has good water resistance; the emulsified state of the emulsion composition is maintained stable even when a water-soluble resin resulting from neutralization with an amine or ammonia or a water-soluble solvent is added to it; and that film-forming adjuvants can be added to it.

The water-soluble resin used as a dispersion stabilizer, however, does not generally have a uniform molecular weight. The water-soluble resin contains a considerable amount of a component having a relatively low molecular weight. Because a film prepared from an emulsion composition containing such a water-soluble resin as a dispersion stabilizer tends to undergo bleeding of the low-molecular-weight component to its surface, the surface of the film exhibits a tacky feel over an extended period of time even after curing and has a poor tactile hand. Moreover, when the film is polished, it will be softened by the heat of friction.

An attempt has been made on the other hand to use an oxidation-curable (crosslinkable) water-soluble resin as the dispersion stabilizer. An oxidation-curable emulsion composition containing this oxidation-curable water-soluble resin as a dispersion stabilizer, when oxidized and cured (crosslinked), forms a tough film which is not obtained from a non-crosslinkable emulsion composition. However, since the emulsion composition frequently contains a low-molecular-weight component which is usually difficult to cure by oxidation, or cannot be cured to a completely solid film, it still suffers from the various defects described hereinabove. Because such an oxidation-curable water-soluble resin is intrinsically a soft flexible resin and is solidified completely by oxidation curing, the tackiness of the film and its poor polishing resistance appear outstandingly in the case of oxidation-curable resins.

The present inventors made extensive investigations in order to provide a polymer emulsion which exhibits the characteristic properties of an oxidation-curable resin and which when formulated into a coating composition and coated on a substrate, gives a cured film which is tack-free and has a good feel at the surface and possesses excellent polishability, gloss, gasoline resistance, etc. To achieve this end, they tried to introduce a rigid cellulose derivative having a strong intermolecular cohesive force, such as nitrocellulose, into emulsion particles without destroying the stability of the emulsion.

There is a prior example in which a cellulose derivative is introduced into emulsion particles (see Japanese Laid-Open Patent Publication No. 28188/76 which is a counterpart of U.S. patent application Ser. No. 485,271 filed July 2, 1974), now U.S. Pat. No. 3,953,386.

In this prior technique, an emulsion composition is formed by mixing water, a surface-active agent, at least one polymer (an example of which is a cellulose derivative) and at least one monomer to form an aqueous dispersion of polymer-monomer particles, and then polymerizing the monomer in the particles in the presence of a radical initiator. When a cellulose derivative is used as the polymer component in this method, emulsification of the cellulose derivative-monomer should be performed, prior to the polymerization, to an extent of an emulsion unit, that is, to an average particle diameter of 0.01 to 5 microns. This requires the use of a relatively large quantity of the surface-active agent, which necessarily results in the defect that a film prepared from the resulting emulsion composition has poor water resistance. Furthermore, since the cellulose derivative is rigid, the resulting emulsion composition cannot generally serve as a coating composition unless film-forming adjuvants are added. When a water-soluble film-forming adjuvant is added in a large amount to an emulsion composition obtained by using an ordinary ionic or nonionic low-molecular-weight or high-molecular-weight surface-active substance as a dispersion stabilizer as in the above-cited prior technique, the emulsion system becomes unstable. On the other hand, when a water-insoluble film-forming adjuvant is used in a large amount, the resulting emulsion composition becomes flammable. When it is desired to use the aforesaid emulsion composition as a non-polluting paint instead of an organic solvent-base paint in fields where solvent-base paints are used, a film from the emulsion composition must be made very dense, and for this purpose, a water-soluble resin is generally mixed with the emulsion composition. The emulsion system, however, becomes very unstable in the presence of a neutralizing agent and a water-soluble organic solvent contained in this water-soluble resin. Because of these defects, the emulsion composition in the above-cited prior technique has not gained commercial acceptance.

Accordingly, we attempted to introduce a cellulose derivative into polymer emulsion particles by using as a dispersion stabilizer a water-soluble resin free from the aforesaid defects of ordinary ionic or nonionic low-molecular-weight or high-molecular-weight surface-active substances, and emulsion-polymerizing emulsified particles of the cellulose derivative radical-polymerizable unsaturated monomer. We found that this cannot be achieved by using conventionally known water-soluble resins directly as a dispersion stabilizer, but that a water-soluble resin having compatibility with a cellulose derivative in which a hydrophilic group is spaced as far as possible from a non-hydrophilic group, particularly an oxidation-curable water-soluble resin, undergoes grafting reaction with the radical-polymerizable unsaturated monomer during the emulsion polymerization to provide a polymer emulsion composition which retains the inherent properties of an oxidation-curable emulsion and in which the grafted compound is well entangled with the cellulose derivative to impart very good dispersion stability. It has been specifically found that when this polymer emulsion composition is formulated into a coating composition and coated on a substrate, it gives a coated film having a tack-free surface of good feel because the strong intermolecular cohesive force of the cellulose derivative attracts the low-molecular-weight oxidation-curable resin component having tackiness, and moreover, the coated film has excellent polishability, gloss, gasoline resistance, etc. The above discovery has led to the accomplishment of the present invention.

Thus, according to the present invention, there is provided an oxidation-curable emulsion composition containing a cellulose derivative which is prepared by polymerizing in emulsion a mixture composed of at least one radical-polymerizable unsaturated monomer and at least one cellulose derivative in the presence of an oxidation-curable water-soluble resin.

The cellulose derivative to be introduced into polymer emulsion particles should give a coated film having a tack-free surface of good feel and also possessing superior polishability and other properties when the resulting polymer emulsion composition is coated on a substrate. The cellulose derivative capable of achieving this purpose includes ester-modified and ether-modified cellulose derivatives which have a rigid main chain, a strong intermolecular cohesive force, and a number average molecular weight of generally about 3,000 to about 200,000, preferably about 5,000 to about 50,000. Desirably, these cellulose derivatives have compatibility with the oxidation-curable water-soluble resin, and/or with the grafted product formed between the oxidation-curable water-soluble resin and the radical-polymerizable unsaturated monomer formed by the emulsion polymerization. Since, in practice, the available types of cellulose derivatives are limited, it is the general practice to choose oxidation-curable water-soluble resins which are compatible with the cellulose derivatives to be used in combination.

Typical examples of the ester-modified cellulose derivatives are nitrocellulose, cellulose acetate butyrate, cellulose acetate propionate, cellulose acetate phthalate, acetyl cellulose, cellulose propionate, cellulose butyrate, cellulose phosphate, and cellulose sulfate. Those having an average degree of esterification of generally 15 to 70%, especially 20 to 60%, are preferred.

Typical examples of the ether-modified cellulose derivatives include methyl cellulose, ethyl cellulose, butyl cellulose, benzyl cellulose, carboxy methyl cellulose, carboxy ethyl cellulose, aminoethyl cellulose, hydroxyethyl cellulose, oxyethyl cellulose, hydroxypropyl cellulose, and hydroxypropyl methyl cellulose. Those having an average degree of etherification of generally 30 to 70%, especially 35 to 60%, are preferred.

Nitrocellulose and cellulose acetate butyrate are especially preferred because of their excellent weatherability and moderate price.

The above-exemplified cellulose derivatives may be used singly or in combination with each other.

The term "oxidation-curable water-soluble resin", as used herein, encompasses water-soluble resins which are composed mainly of maleinized polydienes and resins modified with oxidation-curable drying oil fatty acids or semi-drying oil fatty acids, and have the property of oxidatively curing at room temperature to give a coated film having sufficient durability. The maleinized polydiene contains at least 10% by weight, preferably at least 30% by weight, of a diene monomer unit. The resin modified with a drying oil fatty acid or a semi-drying oil fatty acid contains the drying oil fatty acid or semi-drying oil fatty acid in an oil length of at least 5, preferably at least 10. The oxidation-curable water-soluble resins have a number average molecular weight of about 500 to about 50,000, preferably about 800 to about 15,000 and an acid value of about 20 to about 350, preferably about 50 to about 200. These water-soluble resins may by themselves be used as film-forming resins. Hence, these water-soluble resins can be clearly distinguished from the conventional ionic or nonionic low-molecular-weight or high-molecular-weight surfactants. Known oxidation-curable water-soluble resins may be used in the present invention. Typical examples are shown below.

(i) Maleinized polydienes

They are prepared by maleinizing in a customary manner homopolymers or copolymers of diene compounds having 4 to 8 carbon atoms (containing at least 10% by weight, preferably at least 30% by weight of diene units). Polybutadiene and butadiene copolymers are preferred as the polydienes. Polybutadiene and butadiene copolymers containing at least 20% by weight, especially 60 to 100% by weight, of a 1,2-vinyl structure are especially preferred. Known ordinary monomers such as styrene, α-methylstyrene, vinyltoluene, acrylic esters, methacrylic esters, acrylonitrile and methacrylonitrile are useful as comonomers for production of copolymers of the diene compounds.

These maleinized polydienes are described, for example, in the specification of Japanese Patent Publication No. 13192/76 which relates to the production of a vinyl polymer emulsion by the emulsion polymerization of a polymerizable vinyl monomer using the maleinized polydiene as a dispersion stabilizer. Examples of preferred maleinized polydiene disclosed there include maleinized polybutadiene having an acid value of 190 obtained by reacting polybutadiene having a molecular weight of 1,100 and composed of 89.2% of 1,2-vinyl type diene units and 10.8% of 1,4-trans type diene units with maleic anhydride, and a maleinized butadiene copolymer having an acid value of 162 obtained by reacting a 1,2-vinyl type butadienestyrene copolymer (butadiene content 80%) having a molecular weight of 2,000 to 2,400 with maleic anhydride.

This maleinized polybutadiene finds a wide range of application because it has strong oiliness and excellent grafting ability. But it is not so suitable when nitrocellulose having high polarity is used as the cellulose derivative.

Generally, the degree of maleinization of the maleinized polydiene can be adjusted to the one represented by an acid value of 20 to 350, preferably 50 to 200.

(ii) Maleinized fatty acid-modified alkyd resins

Drying oil fatty acids or semi-drying oil fatty acids are used as modifying fatty acids. These modified alkyd resins can be obtained by maleinizing in a customary manner known fatty acid-modified alkyl resins having an oil length of generally at least 20, preferably at least 40. The degree of maleinization at this time can be adjusted to the one represented by an acid value of 20 to 300, preferably 50 to 150.

Examples of the drying oil fatty acids or semi-drying oil fatty acids for modifying the alkyd resins include safflower oil fatty acid, linseed oil fatty acid, soybean oil fatty acid, sesame oil fatty acid, poppyseed oil fatty acid, perilla oil fatty acid, hempseed oil fatty acid, grape kernel oil fatty acid, tall oil fatty acid, sunflower oil fatty acid, cotton seed oil fatty acid, walnut oil fatty acid, rubber seed oil fatty acid, tung oil fatty acid, oiticica oil fatty acid, dehydrated castor oil fatty acid, and Hidiene fatty acid (a trademark for a conjugated fatty acid made by Soken Kagaku Co., Ltd. Japan).

The alkyd resins include, for example, those obtained by condensing a polyhydric alcohol component such as ethylene glycol, propylene glycol, diethylene glycol, butylene glycol, glycerol, trimethylolethane, trimethylolpropane, pentaerythritol and sorbitol and a polybasic acid component such as phthalic anhydride, isophthalic acid, terephthalic acid, trimellitic acid, tetrahydrophthalic anhydride, succinic acid, adipic acid, and sebacic acid.

(iii) Maleinized fatty acid-modified epoxy resins

Suitable maleinized fatty acid-modified epoxy resins are prepared by maleinizing in a customary manner fatty acid-modified epoxy resins having an oil length of generally at least 20, preferably at leat 40, obtained by the addition reaction between an epoxy resin resulting from the reaction of bisphenol A with epichlorohydrin or -methylepichlorohydrin and a drying oil fatty acid or semi-drying oil fatty acid of the type exemplified in (ii) above. The degree of maleinization may be adjusted to the same degree as in (ii) above.

(iv) Fatty acid-modified acrylic resins

They are obtained, for example, by reacting a hydroxyl- or glycidyl-containing acrylic monomer (e.g., hydroxyethyl acrylate, hydroxyethyl methacrylate, hydroxypropyl acrylate, hydroxypropyl methacrylate, glycidyl acrylate, or glycidyl methacrylate) with a drying oil fatty acid or semi-drying oil fatty acid of the type exemplified in (ii) above, and copolymerizing the resulting product with an $\alpha,\beta$-ethylenically unsaturated carboxylic acid (e.g., acrylic acid, methacrylic acid, crotonic acid, itaconic acid, maleic acid, maleic anhydride, or fumaric acid) and/or another unsaturated monomer (e.g., methyl acrylate, ethyl acrylate, propyl acrylate, butyl acrylate, methyl methacrylate, ethyl methacrylate, propyl methacrylate, butyl methacrylate, styrene, vinyltoluene, acrylonitrile or methacrylonitrile); or by reacting a glycidyl-containing acrylic monomer with a drying oil fatty acid or semi-drying oil fatty acid, followed by addition reaction of the resulting product with an $\alpha,\beta$-ethylenically unsaturated carboxylic acid copolymer.

These aliphatic fatty acid-modified acrylic copolymers have an oil length of generally at least 5, preferably at least 10.

Such fatty acid-modified acrylic resins are disclosed, for example, in the specification of Japanese Laid-Open Patent Publication No. 108471/77 which relates to the production of a vinyl polymer emulsion by emulsion polymerization of a polymerizable vinyl monomer using the fatty acid-modified acrylic resin as a dispersion stabilizer. A suitable example is a safflower oil fatty acid-modified acrylic resin having an acid value of 82 which is obtained by copolymerizing an addition reaction product of safflower oil fatty acid and glycidyl methacrylate or hydroxyethyl methacrylate, acrylic acid, n-butyl methacrylate and styrene. Since its compatibility with the cellulose derivative can be freely controlled, it is especially preferred in this invention.

(v) Maleinized fatty acid-modified acrylic resins

They are obtained by maleinizing the fatty acid-modified acrylic resins described in (iv) above in a customary manner. The suitable degree of maleinization in this case is the one corresponding to an acid value of 20 to 300, preferably 50 to 150. The fatty acid-modified acrylic resins should have an oil length of generally at least 20, preferably at least 40, in order to maleinize them. The $\alpha,\beta$-ethylenically unsaturated carboxylic acid unit as a constituent element of the acrylic resin is not always necessary, and in this case, modification of the hydroxyl- or glycidyl-containing unsaturated monomer with the drying oil fatty acid or semi-drying oil fatty acid may be performed after the preparation of the copolymer.

(vi) Maleinized fatty acid-modified vinyl resins

Suitable are those obtained by reacting a styrene/allyl alcohol copolymer with the aforesaid drying oil fatty acid or semi-drying oil fatty acid, and maleinizing the reaction product in a customary manner, and having an acid value of 20 to 300, especially 50 to 150.

(vii) Maleinized oils, maleinized stand oils and maleinized boiled oils

These oils are known per se, and those containing linseed oil and soybean oils as an oil component are preferred. They are especially effective when used in combination with cellulose acetate butyrate.

(viii) Water-soluble fatty acid-modified alkyd resins

They may be obtained, for example, by synthesizing an alkyd resin having an excess of hydroxyl groups using a drying oil fatty acid or semi-drying oil fatty acid as a modifying fatty acid, and half-esterifying the hydroxyl groups of the alkyd resin with phthalic anhydride or trimellitic anhydride thereby introducing an acid group; or by esterifying the hydroxyl groups of the alkyd resin with trimellitic acid, leaving one acid group of trimellitic acid; or by using dimethylolpropionic acid as the alkyd resin component and thereby leaving a secondary carboxylic acid group having low reactivity.

(ix) Water-soluble fatty acid-modified urethane resins

They are obtained, for example, by reacting a reaction product of a trivalent or tetravalent alcohol or a diepoxy compound with a drying oil fatty acid or semi-drying oil fatty acid with a diisocyanate, or by reacting a hydroxycarboxylic acid having two hydroxyl groups and one carboxyl group per molecule with a diisocyanate compound. Those having an oil length of 5 to 50 and an acid value of 10 to 150 are generally suitable.

These oxidation-curable resins (i) to (ix) may be modified, as desired, by urethanization, urea-modification, esterification, amidation, grafting, etc. They may be used either singly or as a mixture of two or more.

The oil length of the aforesaid oxidation-curable resin other than the maleinized polydienes (i) is not critical, but is preferably be changed according to the type of the cellulose derivative used. For example, their oil length is not more than 65, preferably 10 to 60, when they are used in combination with cellulose derivatives not containing alkyl groups having at least 4 carbon atoms (e.g., the butyl group), such as nitrocellulose and acetyl cellulose. When they are used in combination with cellulose derivatives having an alkyl group with at least 4 carbon atoms (e.g., butyl group), such as cellulose acetate butyrate, the oil length of the oxidation-curable resins may be in the same range as in the case of nitrocellulose and acetyl cellulose. But when the content of the butyl group is relatively large, it is advantageous that the oxidation-curable resins have a large oil length of usually at least 8, preferably 15 to 75.

The fatty acid-modified acrylic resins (iv) are especially preferred for obtaining the emulsion composition of this invention.

The above oxidation-curable resins can be used as a dispersion stabilizer in accordance with this invention after they are subjected to neutralization treatment using a known neutralizing agent, preferably a volatile amine and ammonia, and if desired, rendered water-soluble using a water-soluble organic solvent (such as Cellosolve-type solvents and alcohol solvents).

The "radical-polymerizable unsaturated monomer" used in the preparation of the polymer emulsion in this invention may be any radical-polymerizable unsaturated monomer which has compatibility with the oxidation-curable water-soluble resin and the cellulose derivative, does not undergo excessive grafting reaction, and does not extremely inhibit polymerization. Generally, vinyl aromatic monomers, acrylic monomers and olefinic monomers are suitable. Specific examples are given below.

(a) Vinyl aromatic compounds

Vinylbenzene derivatives having 8 to 10 carbon atoms such as styrene, α-methylstyrene and vinyltoluene; and vinyl heteroaromatic compounds such as vinylpyridine.

(b) Acrylic or methacrylic esters $C_{1-20}$ alkyl or cycloalkyl esters of acrylic acid or methacrylic acid, such as methyl acrylate, ethyl acrylate, propyl acrylate, isopropyl acrylate, butyl acrylate, hexyl acrylate, octyl acrylate, lauryl acrylate, cyclohexyl acrylate, methyl methacrylate, ethyl methacrylate, propyl methacrylate, isopropyl metharylate, butyl methacrylate, hexyl metharylate, octyl methacrylate, lauryl methacrylate and cyclohexyl methacrylate; addition condensation products between glycidyl acrylate or glycidyl methacrylate and $C_{2-18}$ monocarboxylic acid compounds (such as actetic acid, propionic acid, oleic acid, stearic acid and lauric acid); alkoxyalkyl esters of acrylic acid or methacrylic acid such as methoxybutyl acrylate, methoxybutyl methacrylate, methoxyethyl acrylate, methoxyethyl methacrylate, ethoxybutyl acrylate, and ethoxybutyl methacrylate; alkenyl esters of acrylic acid or methacrylic acid such as allyl acrylate and allyl methacrylate; and condensation products between $C_{2-8}$ hydroxyalkyl esters of acrylic or methacrylic acid such as hydroxyethyl acrylate, hydroxyethyl methacrylate, hydroxypropyl acrylate or hydroxypropyl methacrylate and $C_{2-26}$ monocarboxylic acid compounds.

(c) Polyenes, especially dienes, having 2 to 8 carbon atoms such as butadiene, isoprene and chloroprene (d) Vinyl esters of carboxylic acids such as vinyl acetate and Veova monomer (a product of Shell Chemical Co.).

The vinyl aromatic compounds and acrylic or methacrylic esters are especially preferred in this invention.

The unsaturated monomer is properly selected depending upon the desired properties of the final emulsion composition. These monomers may be used singly or as a mixture of two or more. It may also be used in combination with not more than 50% by weight, preferably not more than 30% by weight, based on the total weight of the monomers used, of a hydrophilic unsaturated monomer. Examples of such hydrophilic unsaturated monomers include 2-hydroxyethyl acrylate, 2-hydroxyethyl methacrylate, 2-hydroxypropyl acrylate, 2-hydroxypropyl methacrylate, acrylonitrile, methacrylonitrile, acrylic acid, methacrylic acid, glycidyl acrylate, glycidyl methacrylate, acrylamide, N-n-butoxymethyl acrylamide, vinylpyridine, N-methylolacrylamide and methacrylamide. They may be used as a mixture of two or more.

In addition to the above monomers, dimethyl maleate, dibutyl maleate, monomethyl maleate, and monobutyl maleate which are difficult of radical polymerization when used alone may also be used.

According to this invention, a mixture of the radical-polymerizable unsaturated monomer and the cellulose derivative is polymerized in emulsion in the presence of the oxidation-curable water-soluble resin used as a dispersion stabilizer.

To perform the emulsion polymerization, usually known procedures may be used. For example, it is carried out at a temperature ranging from the freezing point to the boiling point of water with stirring or in a stationary condition in the presence of the dispersion stabilizer and if required, a polymerization initiator (such as an azo compound, peroxide compound, diazo compound, nitroso compound, sulfide, or redox system).

Water and a mixture of water and a water-miscible organic solvent (such as alcohols, Cellosolves, carbitols, ethers, diglymes, glycols, etc.) may be used as an aqueous medium which acts as a reaction medium for the above polymerization.

In order to improve dispersion of the cellulose derivative in the above emulsion polymerization procedure, the cellulose derivative is dissolved in the unsaturated monomer in advance, and after reducing the viscosity of the solution, it is dispersed in the oxidation-curable water-soluble resin; or a mixed solution of the three components is dispersed in water and then used in the emulsion polymerization. This is preferred because the amount of the solvent used can be decreased.

The amount of the oxidation-curable water-soluble resin used as a dispersion stabilizer may be generally 3 to 85% by weight, preferably 10 to 60% by weight, based on the total solids content (resin content) of the resulting emulsion.

The amount of the cellulose derivative to be introduced into the resulting emulsion particles is usually 5 to 65% by weight, preferably 8 to 50% by weight, based on the total solids content (resin content) of the resulting emulsion.

The unsaturated monomer is used in an amount of usually 10 to 92% by weight, preferably 20 to 82% by weight, based on the total solids content (resin content) of the resulting emulsion.

The oxidation-curable emulsion composition containing the cellulose derivative produced by the present invention is usually semi-transparent and may consist of emulsion particles having an average particle diameter of generally not more than 1 micron, preferably not more than 0.5 micron. The oxidation-curable water-soluble resin used as a dispersion stabilizer undergoes graft polymerization with the radical-polymerizable unsaturated monomer during the emulsion polymerization and is fixed to the emulsion particles. Moreover, the emulsion polymerization is carried out in the place where the cellulose derivative introduced is present. Accordingly, the resulting grafted product is well entangled with the cellulose derivative, and the resulting emulsion has excellent dispersion stability.

The resulting oxidation-curable emulsion composition containing the cellulose derivative can be used as a film-forming component of a coating composition either as such or optionally after its viscosity is adjusted to a value suitable for coating. If required, the emulsion composition may contain another water-soluble resin, an extender pigment, a coloring pigment, a dryer (e.g., cobalt naphthenate or lead naphthenate), a rust inhibitor, a plasticizer, an organic solvent, etc. in amounts usually employed.

Because in the emulsion composition of this invention, the cellulose derivative which is rigid and has a strong intermolecular cohesive force is included in the emulsion particles, an oxidation-cured film prepared from it has a tack-free surface of excellent tactile hand as a result of the low-molecular-weight component that may be present therein being attracted by the cellulose derivative.

Furthermore, since the emulsion composition of this invention contains the rigid cellulose derivative, a coated film prepared from it has excellent polishability and excellent gasoline resistance and other properties.

Moreover, the emulsion composition of this invention exhibit excellent oxidation-curability at room temperature because oxidation-curable resins modified with drying oil fatty acids or semi-drying oil fatty acids, maleinized polydienes, etc. are used as a dispersion stabilizer.

Thus, a coated film prepared from the emulsion composition of this invention fully cures even at room temperature. It may, if desired, be cured by heating, and this makes it easy to obtain a cured tack-free film.

The emulsion composition of this invention may be used singly or in combination with another water-soluble or water-dispersible resin in versatile paints. It can also be used in industrial paints. It is also useful for resin treatment or as an adhesive.

The following Examples illustrate the present invention more specifically. All percentages in these examples are by weight.

EXAMPLE 1

A 2-liter four-necked flask was charged with 500 g of butyl Cellosolve and 130 g of acetone, and they were heated to 85° C. A mixture consisting of 80 g of ethyl acrylate, 180 g of methyl methacrylate, 103 g of acrylic acid, 267 g of a condensate of hydroxyethyl methacrylate and safflower oil fatty acid and 32 g of azobisdimethylvaleronitrile was added dropwise over the course of 2 hours. During this time, the reaction temperature rose to 100° C. Then, while maintaining the temperature at 100° C., 5.2 g of azobisisobutyronitrile was added twice, i.e. 1 hour and 2 hours after the above dropwise addition, and the mixture was allowed to stand for 2 hours. After the reaction, acetone and a part of the butyl Cellosolve were removed by distillation under reduced pressure. Thus, there was obtained a water-solubilizable oxidation-curable resin solution having a resin acid value of 119 and a solids content of 58.8%.

The resulting resin solution (272 g), 331 g of n-butyl methacrylate and 118 g of nitrocellulose wetted with 30% isopropyl alcohol (FQ type SS ¼, a product of Daicel Ltd.) were mixed and dissolved, and 22 cc of aqueous ammonia and 724 g of water were added to the solution. The mixture was dispersed for 30 minutes by a homomixer. The resulting aqueous dispersion was put into a 2-liter four-necked flask, and a solution of 1 g of ammonium persulfite in 10 g of water was added. The mixture was heated at 80° C. for 3 hours. One hour after the heating, 1 g of Kayabutyl H-70 (tert-butyl hydroxyperoxide, a product of Nippon Kayaku Co., Ltd.) was added as an additional catalyst to afford a nitrocellulose-containing oxidation-curable emulsion composition having a solids content of 39.3%, a viscosity of 7,200 centipoises (determined at 30 rpm by a Brookfield viscometer; the same measuring method applies hereinbelow) and a transparency (expressed by the thickness of an emulsion layer through which a 12-point type kept in close contact with a transparent glass plate can be read; the same measuring method applies hereinbelow) of 0.48 mm.

When the resulting emulsion composition was coated on a glass plate, a completely transparent film having a gloss of 125 (measured by 20° mirror surface reflection; the same method of measurement applies hereinbelow) was obtained. When the coated film was dried for 1 day at room temperature, it showed a pencil hardness of HB. The properties of the coated film measured after drying it for 7 days are shown in Table 1.

EXAMPLE 2

An oxidation-curable emulsion composition was prepared by the same method and the same recipe as in Example 1 except that dispersion by the homomixer was replaced by gentle stirring in the four-necked flask. The solids content and the condition of a coated film of the resulting emulsion composition were the same as in Example 1. After drying for 7 days, the coated film showed the properties given in Table 1.

EXAMPLE 3

A 62% butyl Cellosolve solution (302 g) of the oxidation-curable water-soluble resin produced in Example 1, 290 g of n-butyl methacrylate and 177 g of nitrocellulose wetted with 30% isopropyl alcohol (FQ type SS ¼, a product of Daicel Ltd.) were mixed and dissolved, and 22 cc of aqueous ammonia and 724 g of water were added to the solution. The mixture was dispersed for 30 minutes using a homomixer. During this time, some amount of water was added in order to adjust the viscosity of the solution. The resulting aqueous dispersion was put into a 2-liter four-necked flask, and a solution of 1 g of ammonium persulfite in 10 g of water was added to the aqueous dispersion. The mixture was heated at 80° C. for 3 hours. One hour after the heating, 1 g of Kayabutyl H-70 (the same as in Example 1) was added as an additional catalyst. Thus, there was obtained a nitrocellulose-containing oxidation-curable emulsion composition having a solids content of 38.8%, a viscosity of 6,000 centipoises and a transparency of 1.5 mm (semi-transparent).

When this emulsion composition was coated on a glass plate, a completely transparent film having a gloss of 143.1 was obtained. After drying at room temperature for 1 day, the film showed a pencil hardness of HB. The properties of the film after drying for 7 days are shown in Table 1.

EXAMPLE 4

A 2-liter four-necked flask was charged with 500 g of butyl Cellosolve and 130 g of acetone, and they were heated to 85° C. Then, a mixed solution of 360 g of isobutyl methacrylate, 103 g of acrylic acid, 281 g of the same condensate of hydroxyethyl methacrylate and safflower oil fatty acid as used in Example 1 and 32 g of azobisvaleronitrile was added dropwise over the course of 2 hours. During this time, the reaction temperature rose to 100° C. Then, while the temperature was maintained at 100° C., 5.2 g of azobisisobutyronitrile was added one hour and two hours later, respectively. The mixture was further heated at 100° C. for 2 hours. After the reaction, the acetone and a part of butyl Cellosolve were removed. Thus, a water-solubilizable oxidation-curable resin having a solids content of 66.5% and an acid value of 112 was obtained. Then, 240 g of the resulting resin solution, 32 g of butyl Cellosolve, 331 g of n-butyl methacrylate and 83 g of cellulose acetate butyrate (EAB-381 0.1; Eastman Chemical Co.) were mixed and dissolved, and 22 cc of aqueous ammonia and 759 g of water were added. The mixture was dispersed for 30 minutes by a homomixer. The resulting aqueous dispersion was put into a 2-liter four-necked flask, and a solution of 1 g of ammonium peroxide in 10 g of water was added, and the mixture was heated at 80° C. for 3 hours. One hour after the heating, 1 g of Kayabutyl H-70 (same as in Example 1) was added as an additional catalyst. Thus, a cellulose acetate-containing oxidation-curable emulsion composition having a solids content of 38.5% and a viscosity of 80 centipoises was obtained.

When the emulsion composition was coated on a glass plate, a completely transparent film having superior gloss was obtained at room temperature. After drying for 1 day at room temperature, the film showed a pencil hardness of 2B. The properties of the film after drying for 7 days are shown in Table 1.

EXAMPLE 5

An emulsion composition having a solids content of 38.5% and a viscosity of 30 centipoises were prepared by the same method and recipe as in Example 4 except that cellulose acetate butyrate (CAB-551 0.2; Eastman Chemical Co.) was used instead of the cellulose acetate butyrate used in Example 4. When this emulsion composition was coated on a glass plate, a transparent film having gloss was obtained at room temperature. After drying for 1 day, the film showed a pencil hardness of B. The properties of the film after drying for 7 days are shown in Table 1.

EXAMPLE 6

Maleinized polybutadiene (160 g) having an acid value of 100 and obtained by maleinizing 1,2-vinyl type polybutadiene having a number average molecular weight of 3,000 in a customary manner, 100 g of butyl Cellosolve, 331 g of n-butyl methacrylate and 83 g of cellulose acetate butyrate (CAB-551 0.2; Eastman Chemical Co.) were mixed and dissolved, and 19 cc of aqueous ammonia and 727 g of water were added. The mixture was dispersed for 30 minutes by a homomixer. The resulting aqueous dispersion was put into a 2-liter four-necked flask, and a solution of 1 g of ammonium peroxide in 10 g of water was added, and the mixture was heated at 80° C. for 3 hours. There was obtained oxidation-curable emulsion composition containing cellulose acetate butyrate and having a solids content of 40.1% and a viscosity of 7,400 centipoises.

When this emulsion composition was coated on a glass plate, a transparent film having gloss was obtained at room temperature. After drying for 1 day, the coated film showed a pencil hardness of B. The properties of the film after drying for 7 days are shown in Table 1.

EXAMPLE 7

A reactor was charged with 482 g of pentaerythritol, 417 g of isophthalic acid, 1,541 g of linseed oil fatty acid, 361 g of benzoic acid, 150 g of xylene and 5.6 g of dibutyltin oxide, and they were heated at 240° C. in the prsence of nitrogen until the product had an acid value of 2.9. Then, 278 g of maleic anhydride was added to the product and reacted with it at 200° C. for 3 hours in the presence of nitrogen. After the reaction, the unreacted maleic anhydride and xylene were removed from the reaction system by distillation under reduced pressure. Then, 70 parts of water was added to effect ring-opening reaction of the acid anhydride group. Then, n-butyl Cellosolve was added to the reaction product to afford a water-soluble oxidation-curable resin solution having a solids content of 80.7% and a resin acid value of 86.8.

Then, 120 g of the resin solution, 36 g of n-butyl Cellosolve, 166 g of n-butyl methacrylate and 60 g of nitrocellulose wetted with 30% of isopropyl alcohol; FQ type SS ¼, a product of Daicel Ltd.) were mixed and dissolved, and 11 cc of aqueous ammonia and 363 g of water were added to the solution. The mixture was well dispersed by a homomixer. A solution of 0.5 g of ammonium persulfite in 5 g of water was added, and the mixture was heated at 80° C. for 3 hours. One hour after the heating, 1 g of Kayabutyl H-70 was fed as an additional catalyst. Thus, a nitrocellulose-containing oxidation-curable emulsion composition having a solids content of 38.5% and a viscosity of 3200 centipoises was obtained.

The resulting emulsion composition was coated on a glass plate, and dried at room temperature for 7 days. The properties of the resulting coated film are shown in Table 1.

EXAMPLE 8 a nitrocellulse-containing oxidation-curable emulsion composition was prepared in the same way as in Example 1 except that 83 g of styrene, 166 g of n-butyl acrylate and 83 g of tert-butyl methacrylate were used instead of 331 g of n-butyl methacrylate used in Example 1. The resulting emulsion composition had a solids content of 38.0% and a viscosity of 1,000 centipoises.

When the composition was coated on a glass plate, a completely transparent film having gloss was obtained. After drying at room temperature for 1 day, the film showed a pencil hardness of B. The properties of the film after drying for 7 days are shown in Table 1.

COMPARATIVE EXAMPLE 1

An emulsion composition was prepared in the same way as in Example 1 except that n-butyl methacrylate was added in the same amount instead of the wetted nitrocellulose in Example 1. The resulting emulsion composition had a solids content of 39.5%. When the emulsion composition was coated on a glass plate, a transparent film having much gloss was obtained, and after drying at room temperature for 1 day, showed a pencil hardness of 5B. The properties of the coated film after drying for 7 days are shown in Table 1.

COMPARATIVE EXAMPLE 2

A reactor was charged with a solution A consisting of 161.0 g of methyl methacrylate, 161.0 g of 2-ethylhexyl acrylate, 4.7 g of methacrylic acid, 194.0 g of nitrocellulose used in Example 1, 4.8 g of octylphenoxypolyethoxyethanol and 11.7 g of polyethoxysorbitan monostearate, and a solution B consisting of aralkyl sulfonate (Ultrawet DS, a product of ARCO), 10.7 g of phosphate ester (Gafac RE-610, a product of General Aniline and Film Corporation) and 199 ml of water. The resulting mixture was dispersed for 15 minutes by a homomixer. The dispersion was diluted with 100 ml of water, followed by addition of sodium hydrogen carbonate. Water (165 ml) was further added to the aqueous dispersion, and the mixture was heated to 70° C. A solution of 0.5 g of potassium persulfate in 35 ml of water was added at a rate of 0.5 ml/min. for 45 minutes. Then, the remaining initiator solution was added, and the temperature was maintained at 74° to 81° C. for 30 minutes. Thus, an emulsion composition having a solids content of 46% was obtained.

When 10% of butyl Cellosolve was added to the emulsion composition, its viscosity increased and "seeding" occurred. "Seeding" also occurred when 1% of triethylamine was added. Thus, the emulsion composition was very unstable when a water-soluble solvent and a neutralizing agent are were added.

To 100 parts of the resulting emulsion composition were added 20 parts of butyl carbitol acetate and 6 parts of dibutyl adipate. The resulting mixture formed a transparent coated film. The properties of the coated film are shown in Table 1. The emulsion composition, on storage for 7 days, solidified.

TABLE 1

| Properties of the Coated film (*2) | Example and Comparative Example (*1) | | | | | | | | | |
|---|---|---|---|---|---|---|---|---|---|---|
| | Example | | | | | | | | Comparative Example | |
| | 1 | 2 | 3 | 4 | 5 | 6 | 7 | 8 | 1 | 2 |
| Pencil hardnes | F | F | H | HB | F | F | B | HB | B | 6B |
| Bending test | O⁻ | O⁻ | O⁻ | O | O | O | O | O | O | O |
| Water resistance | O | O | O | ⓐ | ⓐ | ⊚ | O | O | ⓐ | X |
| Gasoline resistance | O | O | O | ⓐ | ⓐ | O⁻ | ⓐ | O | ⓐ | Δ |
| Gloss | ⊚ | ⊚ | ⊚ | O | O⁺ | O⁻ | O⁻ | O | O | O |
| Tackiness | ⊚ | ⊚ | ⊚ | ⊚ | ⊚ | ⊚ | O | ⊚ | Δ | X |
| Surface touch | ⊚ | ⊚ | ⊚ | ⊚ | ⊚ | O | ⊚ | ⊚ | Δ | Δ |
| Polishability | ⊚ | ⊚ | ⊚ | O | O | O | O | ⊚ | Δ | X |

(*1) The emulsions compositions in Examples 1 to 6 and Comparative Example 1 contained 0.05% of cobalt naphthenate (calculated as the metal), 0.05% of manganese naphthenate (calculated as the metal) and 0.15% of lead naphthenate, all based on the solids content. Coating on an iron plate and a glass plate was effected by using a doctor blade to a thickness of about 20 microns.
(2*) Pencil hardness: The pencil hardness of the film on an iron plate was measured.
Bending Test: The coated film on an iron plate was bended by an angle of 180° by a bending tester using a rod with a diameter of 1 cm, and the bended state was observed.
⊚: normal
O⁻: a crack hard to distinguish with the naked eye is perceived.
Water resistance: Water was placed on the surface of a film coated on an iron plate, and a change in the coated film was observed 2 hours later.
⊚: normal
O: very little whitening
ⓐ: no problem in practice though whitening is perceived
X: complete whitening or dissolution.
Gasoline resistance: Gasoline was placed on the surface of a coated film on a glass plate, and its state after evaporation of the gasoline was observed.
O: good
O: no problem in practice though slightly blurred.
Gloss: Observed visually.
Tackiness: A test sample was placed horizontal in an indirect hot air furnace kept at 70° C. with the coated surface of the sample directed upwardly. Five sheets of gauze, 50 mm² in area, were stacked on the center of the coated surface. A weight having a diameter of 40 mm and weighing 500 g was placed on the center. After standing for 1 hour, the sample was taken out of the furnace, and the gauze was separated from the coated surface. The degree of sticking between the coated surface and the gauze and the trace of the woven texture of the gauzes were examined.
⊚: the gauze drops by its own weight when the coated surface is set vertically.
O: no trace of gauze
Δ: the trace of gauze is slightly left.
X: the trace of gauze is clearly left.
Surface touch: The coated surface was touched by a finger at 20° C. and at a relative humidity of 75%, and the surface touch was examined.
⊚: good feel
O: no problem in practice though feel is a little poor.
Δ: tacky feel.
Polishability: The coated surface was polished 10 times with a #400 water-resistant abrasive paper, and then the state of the abrasive paper was examined. The state in which the coated film does not stick to the abrasive paper is good.
⊚: good
O: no problem in practice though a little sticky
Δ: sticky
X: very sticky.

The results of testing the properties of the coated film were evaluated on a scale of five grades, ⊚, O, ⓐ, Δ and X in which ⓐ to ⊚ show that the coated film is practical, and Δ and X show that the coated film is not practical.

What we claim is:

1. An oxidation-curable emulsion composition containing a cellulose derivative, said composition being prepared by polymerizing in emulsion a mixture consisting of at least one radical-polymerization unsaturated monomer and at least one cellulose derivative in the presence of an oxidation-curable fatty acid-modified, water-soluble acrylic resin.

2. The composition of claim 1 wherein said cellulose derivative is an ester-modified or ether-modified cellulose derivative having a number average molecular weight of about 3,000 to about 200,000.

3. The composition of claim 2 wherein the ester-modified cellulose derivative is nitrocellulose, cellulose acetate butyrate, cellulose acetate pripionate, cellulose acetate phthalate, acetyl cellulose, cellulose propionate, cellulose butyrate, cellulose phosphate or cellulose sulfate.

4. The composition of claim 2 wherein the ester-modified cellulose derivative has a degree of esterification of 15 to 70%.

5. The composition of claim 2 wherein the ether-modified cellulose derivative is methyl cellulose, ethyl cellulose, butyl cellulose, benzyl cellulose, carboxy methyl cellulose, carboxy ethyl cellulose, aminoethyl cellulose, oxyethyl cellulose, hydroxyethyl cellulose, hydroxypropyl cellulose or hydroxypropyl methyl cellulose.

6. The composition of claim 2 wherein the ether-modified cellulose derivatives has a degree of etherification of 30 to 70%.

7. The composition of claim 1 wherein the cellulose derivative is nitrocellulose or cellulose acetate butyrate.

8. The composition of claim 1 wherein the oxidation-curable water-soluble resin has a number average molecular weight of about 500 to about 50,000.

9. The composition of claim 1 wherein the water-soluble oxidation-curable water-soluble resin has an acid value of about 20 to about 350.

10. The composition of claim 1 wherein the fatty acid-modified acrylic resin has an oil length of at least 5.

11. The composition of claim 1 wherein the radical-polymerizable unsaturated monomer is a vinyl aromatic compound, an acrylic or methacrylic ester, a diene, or a vinyl ester of a carboxylic acid.

12. The composition of claim 1 wherein the proportion of the oxidation-curable water-soluble resin is 3 to 85% by weight based on the total solids content of the resulting emulsion composition.

13. The composition of claim 1 wherein the proportion of the cellulose derivative is 5 to 65% by weight based on the total solids content of the emulsion composition.

14. The composition of claim 1 wherein the proportion of the unsaturated monomer is 10 to 92% by weight based on the total solids content of the emulsion composition.

15. A coating composition comprising the emulsion composition of claim 1 as a film-forming component.

* * * * *